United States Patent
Braun et al.

(10) Patent No.: US 9,193,656 B2
(45) Date of Patent: Nov. 24, 2015

(54) PROCESS FOR THE MANUFACTURE OF HALOGENATED PRECURSORS OF ALKENONES AND OF ALKENONES

(71) Applicant: SOLVAY SA, Brussels (BE)

(72) Inventors: Max Josef Braun, Wedemark (DE); Uta Claassen, Hohenhameln (DE); Sara Claessens, Nieuwerkerken (BE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 14/365,734

(22) PCT Filed: Dec. 21, 2012

(86) PCT No.: PCT/EP2012/076745
§ 371 (c)(1),
(2) Date: Jun. 16, 2014

(87) PCT Pub. No.: WO2013/093050
PCT Pub. Date: Jun. 27, 2013

(65) Prior Publication Data
US 2014/0357899 A1    Dec. 4, 2014

(30) Foreign Application Priority Data

Dec. 22, 2011  (EP) .................................. 11195352

(51) Int. Cl.
| | |
|---|---|
| *C07C 45/64* | (2006.01) |
| *C07C 45/45* | (2006.01) |
| *C07C 45/65* | (2006.01) |
| *C07C 45/61* | (2006.01) |
| *C07C 49/255* | (2006.01) |

(52) U.S. Cl.
CPC ............... *C07C 45/64* (2013.01); *C07C 45/455* (2013.01); *C07C 45/61* (2013.01); *C07C 45/65* (2013.01); *C07C 49/255* (2013.01)

(58) Field of Classification Search
CPC .............................. C07C 45/64; C07C 45/455
USPC .......................................... 568/405, 407, 415
See application file for complete search history.

(56) References Cited

U.S. PATENT DOCUMENTS

| | | | |
|---|---|---|---|
| 5,708,175 A | 1/1998 | Koyanagi et al. | |
| 6,428,199 B1 | 8/2002 | Rupaner et al. | |
| 2006/0084813 A1* | 4/2006 | Hausmann et al. | ........... 546/315 |
| 2006/0198771 A1 | 9/2006 | Devic et al. | |
| 2012/0041237 A1 | 2/2012 | Katsuhara et al. | |

FOREIGN PATENT DOCUMENTS

| | | |
|---|---|---|
| WO | 2005063780 A | 7/2005 |
| WO | 2009006217 A1 | 1/2009 |
| WO | 2010002577 A1 | 1/2010 |
| WO | 2010125899 A1 | 11/2010 |
| WO | 2011003854 A1 | 1/2011 |
| WO | 2011003856 A1 | 1/2011 |
| WO | 2012025548 A1 | 3/2012 |

OTHER PUBLICATIONS

D. R. Boomer: "Rotating Disk Apparatus for Reaction Rate Studies in Corrosive Liquid Environments", Review of Scientific Instruments, 1972,. 43, No. 2, p. 225.
Fawcett F S et al: "The chemistry of carbonyl fluoride. I. The fluorination of organic compounds", Journal of the American Chemical Society, American Chemical Society, vol. 84, No. 22, Nov. 20, 1962, p. 4275-4285.

* cited by examiner

*Primary Examiner* — Sikarl Witherspoon

(57) ABSTRACT

Process for preparing a halogenated precursor of an alkenone, which comprises reacting a carboxylic acid halide with a vinyl ether in a liquid reaction medium using an equipment having at least one surface in contact with the liquid reaction medium, wherein said surface consists of a material selected from glass, polytetrafluoroethylene and nickel based metal alloy.

18 Claims, No Drawings

PROCESS FOR THE MANUFACTURE OF HALOGENATED PRECURSORS OF ALKENONES AND OF ALKENONES

This application is a U.S. national stage entry under 35 U.S.C. §371 of International Application No. PCT/EP2012/076745 filed Dec. 21, 2012, which claims priority to European application 11195352.7 filed on 22 Dec. 2011. The entire contents of these applications are explicitly incorporated herein by this reference.

The present invention relates to a process for preparing halogenated precursors of an alkenone, to a process for preparing alkenones from the halogenated precursors obtained thereby, to method for transporting or storing the aforesaid products.

Halogenated alkenones, such as 4-ethoxy-1,1,1-trifluoro-3-butenone (ETFBO), are building blocks in chemical synthesis, as disclosed, for example, in U.S. Pat. No. 5,708,175.

WO-A-2011/003854 in the name of the applicant, the entire contents of which is incorporated by reference into the presents, discloses inter alia manufacture of halogenated precursors of an alkenone, carried out in a ceramic lined vessel.

It is an object of the present invention to provide an improved process for the preparation of halogenated precursors of alkenones. It is another object of the present invention to provide a process for the manufacture of alkenones from the halogenated precursors.

The invention relates consequently to a process for preparing a halogenated precursor of an alkenone, which comprises reacting a carboxylic acid halide with a vinyl ether in a liquid reaction medium using an equipment having at least one surface in contact with the liquid reaction medium, wherein said surface consists of a material selected from a nickel based alloy, containing at least 14% wt. molybdenum relative to the total weight of the alloy and 14% wt. of chromium relative to the total weight of the alloy; glass and polytetrafluoroethylene.

It has been found that the process according to the invention allows for efficient manufacture of halogenated precursors of an alkenone while substantially avoiding corrosion of the equipment used and consequently enhancing the plant life and reducing downtimes. In certain aspects of the invention, it is particularly surprising that the highly reactive reagents and products of the reaction can be processed substantially without unwanted side-reactions in an equipment containing transition metals, which are known to catalyze a lot of chemical reactions. It has also been found, surprisingly, that alpha-CF3-ketones, which can be prone to metal-complexation reactions, can be advantageously prepared in equipment made of certain alloys.

Particular alloys in the sense of this invention correspond to the specifications according to ASME SB-575.

In the process according to the invention, the alloy preferably contains nickel, in an amount from 50 to 71 wt %, relative to the total weight of the alloy. Other components include chromium, preferably in an amount from 14 to 20 wt %, relative to the total weight of the alloy, and molybdenum, preferably in an amount from 14 to 20 wt %, relative to the total weight of the alloy, the remainder of the alloy consisting essentially of other metals, in particular transition metals. Said other metals may contain up to 3% wt. of iron, up to 2% wt. of cobalt and up to 1% wt of manganese, all relative to the total weight of the alloy. More preferably, the alloy is selected from Hastelloy® C alloys, for example from the group consisting of Hastelloy® C4, C22 and C276.

In the process according to the invention, the equipment is generally selected from the group consisting of a vessel, a tube, a nozzle, in particular suitable for feeding of reactants, a tank, a stirrer, a heat exchanger, a distillation column or combinations thereof.

It has been found that in the process according to the present invention for preparing an alkenone can advantageously be carried out in a microreactor, at least partially.

Microreactors are known in the art (cf. e.g. WO 2007/042313 A2, US 2009/0295005 A1, EP 1 481 724 A2, or WO 2007/027785 A2). "Microreactors" as used herein is understood in the broadest technical meaningful sense. In the art often "micromixer" and "microreactor" are used as synonyms. In some cases, however, a microreactor which mixes a plurality of fluids together is called a "micromixer" and a microreactor which causes a chemical reaction during the mixing of a plurality of fluids is called a "microreactor". The microreactor as used herein is a device comprising "micromixers", "microreactors" and combinations of these as used in the art. Preferably, "microreactor" as used herein is a device which comprises components, typically channels or flow ducts, having characteristic/determining geometric dimensions of 1 µm to 2000 µm, and in particular preferable from 10 µm to 1000 µm. A microreactor is typically provided with a reaction channel which leads to a plurality of fine reaction channels or flow ducts. The equivalent diameter obtained in the section of the fine reaction channel is, converted to a circle, several micrometers to several hundreds of micrometers.

Preferably, "microreactor" as used herein includes at least one micromixer, which is preferably used in combination with a further microreactor. Further, the term "microreactor" used herein can be a device, which is referred to in the art as "minireactor", "micro heat exchanger", "minimixer" or "micromixer". Examples of these are microreactors, micro heat exchangers, and T- and Y-mixers, as available by a large number of companies (e.g. Ehrfeld Mikrotechnik BTS GmbH, Institut für Mikrotechnik Mainz GmbH, Siemens AG, CPC-Cellulare Process Chemistry Systems GmbH).

As alternative micromixers, V-type mixers, as available by Forschungszentrum Karlsruhe, split and recombine mixers, e.g. cascade mixers or faceted mixers, as available by Ehrfeld Mikrotechnik BTS GmbH, or caterpillar mixers, e.g. obtainable from the Institut für Mikrotechnik, Mainz, can be used. In these mixers the product streams to be mixed are divided into smaller flows and these smaller flows are repeatedly combined and divided. Further alternative micromixers with a cross-sectional constriction, such as focus mixers or cyclone mixers, or else jet mixers, as described in EP 1 165 224 B1, e.g. obtainable from Synthesechemie, and impingement jet mixers or valve mixers, as described in WO 2005/079964 A1, available from Ehrfeld Mikrotechnik BTS GmbH, can be used. Particular preferred cascade mixers are used as micromixers in the process of the present invention.

In one aspect, substantially all or all the surfaces of the equipment which can come into contact with liquid reaction medium consist of a material selected from glass and alloy in accordance with the invention. In another aspect, at least a part of the surfaces which can come into contact with liquid reaction medium consists of alloy in accordance with the invention. In that case, the parts which consist of alloy in accordance with the invention are preferably located at a place of the equipment which comes into contact with the liquid reaction medium at a feed point of reactants or in the vicinity of such feed point, "vicinity" denoting in particular a distance of from greater 0, in particular at least 0.1 to 50 cm of such feed point.

In the process according to the invention, the liquid reaction medium has generally a temperature from −50° C. to 150° C.

In the process according to the invention, the equipment can be used to manufacture a precursor of an alkenone. In this case, the temperature of the liquid reaction medium is generally from 0° C. to 50° C. Especially in this case, the liquid reaction medium comprises hydrogen chloride and an alkenone.

In the process according to the invention, the equipment can be used to manufacture an alkenone from the precursor of the alkenone. In this case, the temperature of the liquid reaction medium is generally from 50° C. to 150° C.

In a first particular embodiment, the equipment has the surface coated or lined onto a support material. Suitable support materials include, for example, steel. When the surface consists of an alloy in accordance with the invention, the latter may be applied onto the support material by techniques such as coating, spraying or cladding. A surface obtained by coating or cladding is preferred.

When the surface consists of polytetrafluoroethylene, high-density polytetrafluoroethylene is preferably used. The polytetrafluoroethylene is preferably applied onto the support material, in particular steel, by spraying.

In a second particular embodiment, the equipment consists of massive alloy in accordance with the invention, in particular as described above.

The process according to the invention is preferably performed to prepare a halogenated alkenone precursor of formula (I)

wherein $R^1$ represents a C1-C10 alkyl group which is optionally substituted by at least one halogen atom or $R^1$ represents $CF_3$, $CF_2Cl$, $CF_2H$; and $R^2$ represents aryl, substituted aryl, or a C1-C10 alkyl group which is optionally substituted by at least one halogen atom and X represents fluorine, chlorine or bromine wherein an acid halide corresponding to Formula (II): $R^1$—C(O)X (II) in which X represents fluorine, chlorine or bromine and $R^1$ has the meaning given above, is reacted with a vinyl ether corresponding to Formula (III): $CH_2$=C(H)—$OR^2$ (III) in which $R^2$ has the meaning given above.

$R^1$ is often a fluorinated C1-C4 alkyl group. $R^1$ preferably represents methyl, ethyl, n-propyl, isopropyl or methyl, ethyl, n-propyl or isopropyl substituted by at least one fluorine atom. It is especially preferred if $R^1$ represents methyl, ethyl or methyl or ethyl substituted by at least one fluorine atom. $CF_3$, $CF_2H$, $CF_2Cl$, $C_2F_5$, $C_3F_7$ are particularly preferred as $R^1$. $CF_3$, $CF_2Cl$ and $CF_2H$ are more particularly preferred as $R^1$.

$R^2$ can be selected for example from aryl, for example, phenyl, C1-C4 alkyl groups and/or phenyl substituted by halogen atoms. $R^2$ is often a C1-C4 alkyl group. Preferably, $R^2$ represents a linear or branched C1-C4 alkyl group, and particularly preferably $R^2$ represents methyl, ethyl, n-propyl or isopropyl, most preferably a methyl or an ethyl group.

X is preferably selected from fluorine and chlorine, more preferably X is chlorine.

The alkenones which can be prepared from the halogenated alkenone precursors of formula (I) are the alkenones of formula (IV),

$R^1$ and $R^2$ have the same meaning as in formula (I). ETFBO is a particularly preferred alkenone.

In the liquid reaction medium of the manufacture of the precursor of an alkenone generally a content of hydrogen halide in the reaction medium of equal to or lower than 1% wt is maintained. Preferably, this content is maintained equal to or lower than 0.5% wt. When the formation of hydrogen halide is substantially avoided, a content of hydrogen halide in the reaction medium equal to or higher than 0.01% wt albeit equal to or higher than 0.1% wt relative to the total weight of the reaction medium is acceptable.

The process according to this specific embodiment, generally comprises carrying out the reaction at a temperature from 0° C. to 40° C., preferably from 10° C. to 30° C., more preferably at equal to or about 25° C. and most preferably at equal to or about 20° C. If desired, the reaction can also be performed at temperatures below 0° C.; e.g., between 0° C. and −50° C., but the reaction rate is lower. It is preferred to operate at a temperature from 0° C. to 40° C.

In the process according to this specific embodiment, the reaction is preferably carried out in a continuously stirred tank reactor (CSTR).

In a particular aspect said the continuously stirred tank reactor is combined with a plug flow reactor. In that case, generally, at least a part of the liquid reaction medium is withdrawn from the continuously stirred tank reactor and subjected to further reaction in a plug flow reactor. In this case, the CSTR reactor is usually in a turbulent state while the plug-flow reactor can be in a turbulent or laminar flow state.

Particular embodiments of CSTR include reactors which consist of one or more cylindrical or spherical tanks wherein a turbulent state of the liquid reaction medium is created by any of the means described above. When more than one CSTR reactor is used, for example 2, 3 or 4 reactors, it is advantageous to split the feed of vinyl ether so as to feed vinyl ether to each reactor.

Particular embodiments of plug flow reactor are in the form of a cylindrical tube through which the feed enters at one end and exits at the other end.

The addition reaction of the acid halide and the vinyl ether is exothermic. As mentioned above, it is preferably performed at a temperature from 0° C. to 40° C., and thus, the reaction medium is preferably cooled.

In another particular aspect said the continuously stirred tank reactor is combined with a heat exchanger. Said heat exchanger advantageously can remove heat from the reactor during the exothermic reaction. The heat exchanger can be a separated device added to the CSTR or the heat exchanger and the reactor can be combined into a single piece of equipment.

Existing apparatus with intensified heat exchange and compact heat exchanger/reactor (HEX reactor).

By way of illustration, the following devices can be used as heat exchangers, especially when added to the CSTR: double jacket, external and internal coils.

If the heat exchanger is a device separated from the reactor, a part of the reaction medium can be passed through a loop via a heat exchanger or a cooling machine. This is preferably performed continuously.

The stirrers may be single-stage or multistage embodiments, especially those which produce not only a tangential flow component but also an axial flow field. Preferred stirrers are those having 1 to 7 stirring blade stages attached, preferably equidistantly, on the axial stirrer shaft. Examples are blade, anchor, impeller, Pfaudler, disk, helical, bar, finger propeller, sigma, paddle, pitched-blade and coaxial stirrers, such as cross-arm. Multiflow, multipulse countercurrent, Intermig and Interpro stirrers. A suitable reactor is described in U.S. Pat. No. 6,428,199. The reactor described therein has a stirring mechanism, incoming and outgoing lines and a removable head wherein both the incoming and outgoing lines and the stirring mechanism are installed on the reactor floor.

A reactor which can be used in the process of the present invention is described in US patent application publication 2006/0198771 A1. A cylindrical vertical stirred reactor provided with means of injection of gaseous (or liquid) reactants at the bottom, and, as essential parts, centrifugal turbines arranged along a single vertical agitating shaft. The shaft is driven by a geared motor unit which is most often situated either above or below the reactor. The reactor may be equipped with counterbaffles and/or a heat exchanger.

In still another aspect, the process according to the invention is carried out in a microreactor. In this embodiment, the internal surfaces of the microreactor consist preferably of an alloy in accordance with the invention. More information about the reaction of the present invention carried out in a microreactor are contained in PCT/EP2011/064503, the entire contents of which is incorporated herein by reference.

Another apparatus for preparing halogenated precursors of an alkenone is now described.

The apparatus comprises two means, wherein the first means comprises a circulation system with a boiler, pipes filled with Raschig rings, centrifugal pump, tubular reactors each with a pipe. Product can be added or removed (for analysis purposes) before and after each of these reactors. For safety reasons, a further length of pipe with cooler and cold traps is mounted after circulation; wherein the second means is used as a receiver and for the thermolysis of the organic products' precursors to the organic products, for example, from 4-chloro-4-ethoxy-1,1,1-trifluoro-butane-2-one (CETFBO) to ETFBO and comprises ceramic boiler with column pipes with Raschig rings and cooler with take-off.

It is understood that each equipment and apparatus described herein before can comprise a surface consisting of glass or alloy in accordance with the invention, and at least one such surface is present in the equipment used in the process according to the invention.

In one embodiment, which is preferred, the liquid reaction medium for the reaction comprises an alkenone, in particular ETFBO, as a solvent. The alkenone is generally used in an amount of from 50 to 99% by weight, preferably from 60 to 99% by weight, more preferably from 75 to 99% by weight of the alkenone relative to the total weight of the reaction medium.

This embodiment is particularly advantageous for starting up said reaction.

The alkenone comprises preferably additional alkenone which is provided to the reaction from an external source, for example an earlier batch manufacture of alkenone. In one aspect of this embodiment, said reaction is carried out by introducing carboxylic acid halide into said alkenone containing liquid reaction medium, in particular during start-up of the manufacturing process. The formation of the halogenated precursor of the alkenone after introduction of a vinyl ether into the liquid reaction medium comprising the alkenone and the carboxylic acid halide will generally provide a liquid reaction medium containing the halogenated precursor and the alkenone.

It is understood that this embodiment may also be applied for reaction of the same type as reaction described above wherein the vinyl ether is not added to a reaction medium containing carboxylic acid halide, for example, vinyl ether may be dissolved in the alkenone containing reaction medium and carboxylic acid halide is then added to the reaction medium containing vinyl ether and alkenone.

In another embodiment, the liquid reaction medium for the reaction of the carboxylic acid halide with the vinyl ether comprises a halogenated precursor of the alkenone, in particular CETFBO. The halogenated precursor is generally used in an amount of from 50 to 99% by weight, preferably from 60 to 99% by weight, more preferably from 75 to 99% by weight of the halogenated precursor to the total weight of the reaction medium.

In a preferred aspect of this embodiment, the process is carried out in continuous mode. In a continuous process, the content of the halogenated precursor of the alkenone in the liquid reaction medium is generally kept in a range from 50 to 99%, preferably in a range from 60 to 99%, more preferably in a range from 75 to 99% by weight of halogenated precursor relative to the total weight of the reaction medium. This is particularly advantageous for a continuous process operated in steady-state, for example in a continuously stirred tank reactor (CSTR).

In a preferred aspect, the remainder of the liquid reaction medium comprises carboxylic acid halide.

The liquid reaction medium generally contains at least 0.5% by weight, preferably at least 1% by weight of carboxylic acid halide relative to the total weight of the reaction medium. Preferably this content is at least 5% weight. The liquid generally contains less than about 20% by weight of carboxylic acid halide relative to the total weight of the reaction medium. Preferably this content is less than 10% weight. Preferably, the liquid contains 5 to 10% by weight of carboxylic acid halide relative to the total weight of the reaction medium. This particular aspect may also be applied to the different embodiments of the process according to the invention described herein. The reaction can be carried out in the presence of an additional solvent. The term "additional solvent" is understood to denote a solvent different from the reactants, the products of said reaction and the additional alkenone or precursor of the alkenone. The solvent to be used may, for example, be an aromatic hydrocarbon such as benzene, toluene or xylene, an aliphatic hydrocarbon such as pentane or hexane; a halogenated hydrocarbon such as methylene chloride, chloroform or ethylene dichloride or fluorinated hydrocarbons such as 1,1,1,3,3-pentafluorobutane (commercialized by Solvay Fluor GmbH under the trademark Solkane® 365 mfc); or an ether such as diethyl ether, dibutyl ether or tetrahydrofuran. Among them, an aromatic hydrocarbon is preferred. Particularly preferred among them, is benzene or toluene. These solvents may be used alone or in combination as a mixture. If appropriate, the solvent is used usually in an amount of from 1 to 35 parts by weight, preferably from 3 to 16 parts by weight, per part by weight of the carboxylic acid halide. It is however preferred to carry out the reaction in the substantial absence or absence of additional solvent.

In a particular embodiment, the solvent further comprises at least one haloether, for example a chloroether such as chloroethyl-ethyl ether. In this case, the content of haloether in the liquid reaction medium is generally from 0.1 to 5% often from 0.5 to 2% by weight relative to the total weight of the liquid reaction medium. It has been found that haloethers are suitable solvents which can be incorporated in the liquid reaction medium, in particular in the indicated concentration ranges while achieving high productivity and selectivity to halogenated precursor of alkenone. In a continuous process, the content of haloether is preferably maintained in the concentration range indicated here above.

It is more particularly preferred to carry out the reaction in a liquid reaction medium consisting or consisting essentially of alkenone, halogenated precursor of alkenone, carboxylic acid halide and vinyl ether. This embodiment has particular advantages for subsequent process steps such as for example a thermolysis or purification operations.

In the process according to the invention and in the particular embodiments thereof, the molar ratio of acid halide to vinyl ether preferably is from 0.8 to 1.2, and particularly preferably from 0.8:1 to about 1. Most preferably, the molar ratio is about 1.

In the process according to the invention and in the particular embodiments thereof, the vinyl ether is generally introduced into the liquid reaction medium at a rate of from 0.01 to 2 mol/hour/mol of carboxylic acid halide. Preferably this rate is from 0.5 to 1.5 mol/hour/mol of carboxylic acid halide. A rate of about 1 mol/hour/mol of carboxylic acid halide has given good results.

The process according to the invention and the particular embodiments thereof can be carried out batchwise or continuously.

In the process according to the invention and in the particular embodiments thereof, it is especially beneficial, in particular in a continuous process to control the concentration of the vinyl ether in the liquid reaction medium. Generally, this concentration is less than 5% by weight relative to the total weight of the liquid reaction medium. Often the concentration of the vinyl ether in the liquid reaction medium is equal to less than 1% by weight relative to the total weight of the liquid reaction medium. Preferably, this concentration is equal to less than 0.5% by weight relative to the total weight of the liquid reaction medium. Generally, this concentration is at least 0.1% by weight relative to the total weight of the liquid reaction medium.

In one embodiment of the invention, the halogenated precursor of the alkenone which is obtained according to the process of the invention can be used as such. For example, it can be used as solvent, e.g. as solvent in a subsequently performed process according to the present invention.

In another embodiment of the invention, the halogenated precursor of the alkenone which is obtained in the process according to the present invention is dehydrohalogenated by the elimination of hydrogen halide to form the respective alkenone. Consequently, the invention further concerns a process for preparing an alkenone, which comprises (a) reacting a carboxylic acid halide with a vinyl ether to form a halogenated precursor of the alkenone in a liquid reaction medium containing an alkenone or a halogenated precursor thereof, and (b) eliminating hydrogen halide from said precursor to form the alkenone.

In that case, the liquid reaction medium generally comprises hydrogen halide, in particular hydrogen chloride. In the liquid reaction medium of the manufacture of the alkenone generally a content of hydrogen halide in the reaction medium of equal to or lower than 10% wt is maintained. Preferably, this content is maintained equal to or lower than 5% wt. The content of hydrogen halide in the reaction medium of the manufacture of the alkenone is generally equal to or higher than 0.1% wt albeit equal to or higher than 0.5% wt relative to the total weight of the reaction medium.

According to one alternative, the elimination of hydrogen halide is carried out simultaneously during the formation of the halogenated precursor of the alkenone, for example, in the presence of an acid scavenger and/or by thermally inducing the elimination of hydrogen halide. The acid scavenger to be used may, for example, be a nitrogen-containing heterocyclic compound such as pyridine, quinoline or picoline; or a tertiary base such as triethylamine, dimethylaniline, diethylaniline or 4-dimethylaminopyridine. Among them, pyridine, triethylamine, dimethylaniline, diethylaniline or 4-dimethylaminopyridine is preferred. Among them, pyridine is particularly preferred. These acid scavengers may be used alone or in combination as a mixture. If appropriate, the acid scavenger is used in an amount of less than 1 equivalent, preferably less than 0.8 equivalents per mol carboxylic acid halide.

If desired, an additional solvent may be present during the elimination of hydrogen halide. The term "additional solvent" has the same meaning as defined above.

In a first particular embodiment, the carboxylic acid halide is trifluoroacetyl chloride. Preferably, the trifluoroacetyl chloride is fed in liquid state into the reaction medium.

In a second particular embodiment, the carboxylic acid halide is Chlorodifluoroacetyl chloride.

In a third particular embodiment, the carboxylic acid halide is Difluoroacetyl chloride.

In a forth particular embodiment, the carboxylic acid halide is trifluoroacetyl fluoride.

In a fifth particular embodiment, the carboxylic acid halide is (trifluoroaceto)acetyl fluoride.

In a sixth particular embodiment, which is preferred, the process for the preparation of a halogenated precursor of an alkenone and the elimination of hydrogen halide is carried out in the substantial or complete absence of an acid scavenger especially when a carboxylic acid chloride as described herein before is used.

In a seventh particular embodiment, which is preferred, the preparation of the halogenated precursor of the alkenone and the elimination of hydrogen halide is carried out in the substantial or complete absence of additional solvent.

In a eighth particular embodiment, which is preferred, the preparation of the halogenated precursor of the alkenone and the elimination of hydrogen halide is preferably carried out in the substantial or complete absence of an acid scavenger and of additional solvent, as described here before. The sixth to eighth, in particular the eighth particular embodiment can be advantageously combined with any of the first to fifth particular embodiment.

In the sixth to eighth particular embodiments of the process according to the invention, "Substantial absence" typically denotes an optional content of equal to or less than 1% by weight, more particularly equal to or less than 0.5% by weight of acid scavenger and/or solvent relative to the total weight of the reaction medium. "Complete absence" in this context typically denotes a process wherein no voluntary addition of acid scavenger and/or solvent to the reaction medium has been carried out. Typically "complete absence" means that no acid scavenger and/or solvent can be detected in a GC of the reaction medium.

In particular the sixth to eighth particular embodiments of the process according to the invention allow for particularly efficient isolation of, if desired, the halogenated precursor of the alkenone and in particular the desired alkenone as reaction proceeds selectively and separation is facilitated by the limitation albeit substantial absence of components different from the starting material and the products of the reaction.

The invention also concerns a process for the manufacture of an alkenone, comprising (a) the manufacture of a precursor of the alkenone according to the process according to the process described above and (b) at least partially converting the precursor obtained in step (a) into the alkenone, preferably by thermolysis. In the process for the manufacture of an alkenone according to the invention, step (b) is carried preferably out in an equipment comprising a surface consisting of glass, polytetrafluoroethylene or alloy, as described herein before.

More specifically, the invention concerns also a process for preparing an alkenone, which comprises (a) reacting a carboxylic acid halide with a vinyl ether to form a halogenated precursor of the alkenone in a liquid reaction medium containing an alkenone or a halogenated precursor thereof, and (b) eliminating hydrogen halide from said precursor to form the alkenone.

This embodiment of the process according to the invention and the particular embodiments thereof, generally comprises carrying out the reaction of step (a) at a first temperature and carrying out step (b) at a second temperature higher than the first temperature.

The first temperature is generally less than 50° C., often less than 40° C., preferably equal to or less than 30° C. In one aspect, the temperature is preferably equal to or less than about −25° C. The first temperature is generally at least −50° C., often equal to or greater than −40° C., preferably equal to or greater than −30° C.

The second temperature is generally at least 50° C., often equal to or greater than 60° C., preferably equal to or greater than 70° C. The second temperature is generally less than 150° C., often less than 100° C., preferably equal to or less than about 80° C.

The process according to the invention and the particular embodiments thereof, generally comprises carrying out the reaction of step (a) at a first pressure and carrying out step (b) at a second pressure lower than the first pressure.

The first pressure is generally chosen to maintain the reaction medium in the liquid state. For example, if trifluoroacetyl chloride is used as acid halide, the first pressure is advantageously atmospheric pressure at a reaction temperature of equal to or less than about −25° C. The first pressure is advantageously a pressure equal to or greater than about 4, preferably about 5 bar abs to equal to or less than about 10 bar at a reaction temperature of from 20 to 30° C.

The second pressure is preferably chosen to allow for fractional distillation at least of the alkenone from the reaction medium. A typical second pressure is from 1 to about $10^{-3}$ bar abs.

The invention also concerns a method for storing or transporting a precursor of an alkenone or an alkenone wherein said storing or transporting is carried out in an equipment comprising a surface consisting of glass, polytetrafluoroethylene or alloy, as described herein before.

The invention also concerns a process for manufacture of an organic compound comprising use of an alkenone or precursor thereof as synthesis intermediate, comprising the process for the manufacture of a precursor of an alkenone or the process for the manufacture of an alkenone according to the invention. Examples of organic compounds which can be produced using the process according to the invention include in particular Sulfoxafluor® or Pyroxolam®, wherein the alkenone produced according to the process according to the invention or the precursor thereof can be suitably further reacted according to the procedures described in WO-A-2005/063780, WO2009006217 and WO2010002577.

Should the disclosure of any patents, patent applications, and publications which are incorporated herein by reference conflict with the description of the present application to the extent that it may render a term unclear, the present description shall take precedence.

The examples here after are intended to illustrate the invention without however limiting it.

Abbreviations:
ETFBO—4-ethoxy-1,1,1-trifluorobut-3-en-2-one
CETFBO—4-chloro-4-ethoxy-1,1,1-trifluorobutan-2-one

EXAMPLE 1

The materials indicated in the table were contacted with Hastelloy® C4 test pieces, having each a weight of between 24.5 g and 24.8 g, at about 20° C. for 6 months. The weight loss was determined.

| Test No. | Material | Wt. difference (g) |
| --- | --- | --- |
| 1 | Neat ethyl vinyl ether (EVE) | 0.0003 |
| 2 | Neat ETFBO | 0.0006 |
| 3 | ETFBO + 50% wt. EVE | 0.0007 |
| 4 | ETFBO saturated with TFAC | −0.0211 |
| 5 | CETFBO | −0.0124 |
| 6 | CETFBO + 50% wt. EVE | −0.0003 |
| 7 | CETFBO saturated with TFAC | 0.0003 |
| 8 | ETFBO saturated with HC1 | −0.0046 |

EXAMPLE 2

CETFBO containing reaction medium is heated to 100° C. in Hastelloy® C4. ETFBO is obtained while the internal surface of the reactor shows no corrosion.

The invention claimed is:

1. A process for preparing a halogenated precursor of an alkenone, which process comprises reacting a trifluoroacetyl halide with a vinyl ether in a liquid reaction medium using an equipment having at least one surface in contact with the liquid reaction medium, wherein said surface consists of a material selected from an nickel based alloy containing at least 14% wt. molybdenum relative to the total weight of the alloy and at least 14% wt. of chromium relative to the total weight of the alloy.

2. The process according to claim 1, wherein the alloy contains at least 50 wt % nickel.

3. The process according to claim 2, wherein the alloy contains nickel, in an amount of 50 to 71 wt %, relative to the total weight of the alloy, chromium, in an amount from 14 to 20 wt %, relative to the total weight of the alloy, and molybdenum, in an amount from 14 to 20 wt %, relative to the total weight of the alloy, the remainder of the alloy consisting essentially of other metals.

4. The process according to claim 1, wherein the equipment is selected from the group consisting of a vessel, a tank, a tube, a distillation column, a stirrer, a microreactor, and combinations thereof.

5. Process according to claim 1, wherein the equipment has the surface coated or lined onto a support material.

6. Process according to claim 1, wherein the equipment consists of massive alloy.

7. Process according to claim 1, wherein the liquid reaction medium comprises hydrogen chloride and optionally an alkenone.

8. Process according to claim 1, wherein the liquid reaction medium has a temperature from 0° C. to 120° C.

9. Process according to claim 1, wherein the trifluoroacetyl halide is trifluoroacetyl chloride and the vinyl ether is selected from methyl-vinyl ether and ethyl-vinyl ether.

10. Process according to claim 1, wherein the liquid reaction medium contains from 1% to less than about 20% by weight of carboxylic acid halide.

11. A process for the manufacture of an alkenone, comprising (a) manufacturing a precursor of the alkenone according to the process according to claim 1 and (b) converting, at least partially, the precursor obtained in step (a) into the alkenone.

12. Process according to claim 11, wherein step (b) is carried out in an equipment comprising a surface, wherein said surface consists of a material selected from an nickel based alloy containing at least 14% wt. molybdenum relative to the total weight of the alloy and at least 14% wt. of chromium relative to the total weight of the alloy.

13. A method for storing or transporting a precursor of an alkenone prepared in accordance with claim 1, the method comprising storing or transporting the precursor in an equipment comprising a surface, wherein said surface consists of a material selected from an nickel based alloy containing at least 14% wt. molybdenum relative to the total weight of the alloy and at least 14% wt. of chromium relative to the total weight of the alloy.

14. A process for manufacture of an organic compound comprising using an alkenone manufactured according to the process of claim 11, or a precursor thereof, as synthesis intermediate.

15. Process according to claim 9, wherein the vinyl ether is ethyl-vinyl ether.

16. Process according to claim 10, wherein the liquid reaction medium contains from 5% to less than about 20% by weight of carboxylic acid halide.

17. The process according to claim 11, wherein the precursor obtained in step (a) is converted, at least partially, into the alkenone by thermolysis.

18. A method for storing or transporting an alkenone manufactured in accordance with claim 11, the method comprising storing or transporting the alkenone in an equipment comprising a surface, wherein said surface consists of a material selected from an nickel based alloy containing at least 14% wt. molybdenum relative to the total weight of the alloy and at least 14% wt. of chromium relative to the total weight of the alloy.

* * * * *